United States Patent
Klein et al.

(10) Patent No.: US 9,726,660 B2
(45) Date of Patent: Aug. 8, 2017

(54) METHOD AND KIT FOR TESTING VARIOUS SELECTED MATERIALS AND/OR SURFACE STRUCTURES FOR CULTURING CELLS

(75) Inventors: Frank Klein, Berlin (DE); Thomas Weigel, Michendorf (DE); Karl Kratz, Berlin (DE); Friedrich Jung, Dresden (DE); Bernhard Hiebl, Berlin (DE); Andreas Lendlein, Berlin (DE); Karola Lützow, Berlin (DE); Andreas Kurtz, Berlin (DE); Petra Reinke, Berlin (DE); Andy R•mhild, Berlin (DE)

(73) Assignee: Helmholtz-Zentrum Geesthacht Zentrum Fur Material und Kustenforschung GMBH, Geesthacht (DE)

( * ) Notice: Subject to any disclaimer, the term of this patent is extended or adjusted under 35 U.S.C. 154(b) by 361 days.

(21) Appl. No.: 13/508,540

(22) PCT Filed: Sep. 24, 2010

(86) PCT No.: PCT/EP2010/064128
§ 371 (c)(1),
(2), (4) Date: Oct. 8, 2012

(87) PCT Pub. No.: WO2011/054601
PCT Pub. Date: May 12, 2011

(65) Prior Publication Data
US 2013/0053276 A1    Feb. 28, 2013

(30) Foreign Application Priority Data
Nov. 9, 2009    (DE) .................. 10 2009 046 525

(51) Int. Cl.
C40B 30/06    (2006.01)
C40B 40/00    (2006.01)
G01N 33/50    (2006.01)

(52) U.S. Cl.
CPC .................. *G01N 33/5008* (2013.01)

(58) Field of Classification Search
CPC .................. C40B 30/06; C40B 40/00
USPC ...................................... 506/10, 13
See application file for complete search history.

(56) References Cited

U.S. PATENT DOCUMENTS

| | | | |
|---|---|---|---|
| 7,457,037 B2 * | 11/2008 | Henry | 359/485.03 |
| 2002/0182720 A1 * | 12/2002 | Gevaert et al. | 435/288.4 |
| 2005/0179156 A1 * | 8/2005 | Carlson et al. | 264/40.1 |
| 2006/0178497 A1 * | 8/2006 | Gevaert et al. | 528/44 |
| 2008/0160539 A1 | 7/2008 | Murphy et al. | |

FOREIGN PATENT DOCUMENTS

| | | |
|---|---|---|
| DE | 19758598 | 4/2000 |
| DE | 102004049758 | 4/2000 |
| WO | WO 03/083044 | 10/2003 |
| WO | WO 03083044 A2 * | 10/2003 |
| WO | WO 2006/116752 | 11/2006 |

OTHER PUBLICATIONS

Hiebl et al., Cytocompatibility testing of cell culture modules fabricated from specific candidate biomaterials using injection molding, Journal of Biotechnology, 148 (2010) 76-82.

Hiebl et al., Cytocompatibility testing of cell culture modules fabricated from specific candidate biomaterials using injection molding, *Journal of Biotechnology* Bd. 148, Nr. 1, Jul. 1, 2010.

* cited by examiner

*Primary Examiner* — Amy M Bunker
(74) *Attorney, Agent, or Firm* — VLP Law Group LLP; Kent H. Cheng

(57) ABSTRACT

The present invention relates to a method for testing different selected materials and/or surface structures for the culture of cells and/or microorganisms.

11 Claims, 1 Drawing Sheet

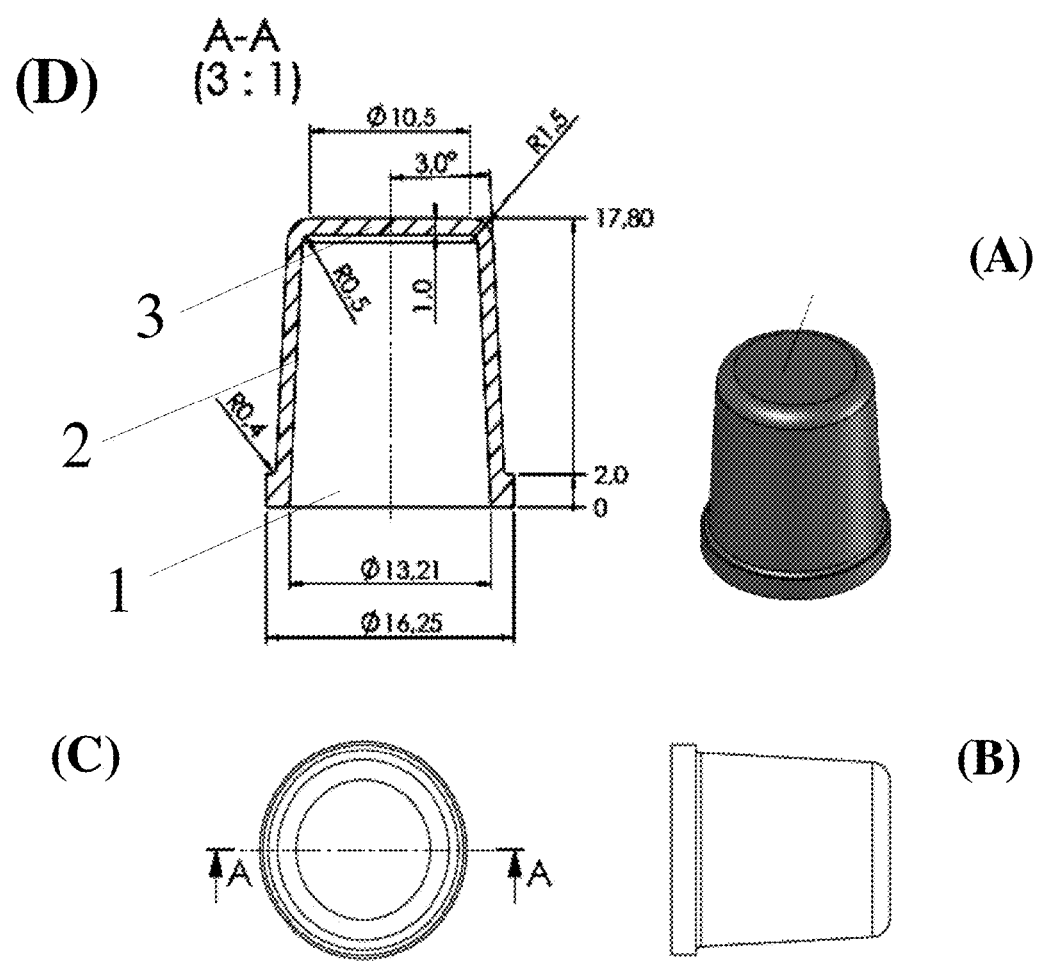

_US 9,726,660 B2_

METHOD AND KIT FOR TESTING VARIOUS SELECTED MATERIALS AND/OR SURFACE STRUCTURES FOR CULTURING CELLS

RELATED APPLICATIONS

This is a U.S. national stage of application No. PCT/EP2010/064128, filed on 24 Sep. 2010. Priority is claimed on the following applications: German Application No.: 10 2009 046 525.1 filed on 9 Nov. 2009, the contents of which are herein incorporated here by reference.

FIELD OF THE INVENTION

In cell culture, the influence of materials which come into any type of contact with the cells to be cultivated plays a key role. For example, new polymer materials are thus being developed and applied in medical engineering, pharmaceutics and biotechnology as a result of testing for compatibility with prokaryotic and/or eukaryotic cells, generally by growing (cultivating) the cells on the new material. It is desirable to provide a system for cell and/or tissue culture which makes it possible to test, in a reproducible, economical and rapid manner, the influence of polymer-based materials on cells in direct contact, without any interference from foreign materials, wherein the system is to be fundamentally suitable for a high-throughput application.

BACKGROUND OF THE INVENTION

Sterile disposable cell culture carriers ("multiwell plates") are used in the field of cell and tissue culture engineering. These carriers are currently produced from few materials, preferably polystyrene PS, and offered for sale. The multiwell plates are commercially available in different forms which are standardised where possible. The cell culture carriers can be sterilised, are preferably suitable for microscopy and are intended to ensure that reproducible tests can be carried out.

Due to new emerging fields of application in the field of medicine, biology or biotechnology (for example cell therapy, tissue engineering, production engineering in the field of biotechnology), the requirements in terms of new materials have increased. In order to test completely new materials, including the modification of materials in terms of chemically or physically induced parameters, such as surface structure, the material is fixed in a cell culture carrier and incubated with cells in liquid cell culture media for a predefined period. So as to fix the materials in the cell culture carrier in a stable manner, the materials are generally supported and weighted down using fixing aids which are produced from a material which differs from the material to be tested and/or the material of the cell culture carrier used (agarose, glass, Teflon, high-grade steel, and polyester, inter alia). The test result is therefore the result of the influence of a plurality of different materials on the cells and can no longer be ascribed merely to one specific material. Furthermore, with the fixing aids it cannot be ruled out with certainty that the form of the materials will not change during the test procedure. For example, the planar structure of films may change to an undulating structure. A considerable change to the microstructured and nanostructured topography of the material may thus result and may have a considerable effect on the interaction between the cells and the material.

The object of the present invention is to overcome or mitigate one or more drawbacks of the prior art. In particular, the object of the invention is to provide a method which allows parallel testing of different materials and surfaces with regard to their suitability for the culture of cells.

SUMMARY OF THE INVENTION

The present invention provides a method for testing different selected materials and/or surface structures for the culture of cells and/or microorganisms, said method comprising the following steps:
 i) providing a plurality of different selected materials and/or surface structures to be tested in the form of beaker-shaped inserts, wherein the beaker-shaped inserts are dimensioned in such a way that each beaker-shaped insert can be inserted in a substantially accurately fitting manner into a well of a multiwell plate suitable for cell culture, wherein each beaker-shaped insert has walls, a base, and an opening in the side facing away from the base, wherein the walls and base of the beaker-shaped inserts are liquid-tight, and wherein each beaker-shaped insert has a selected material and/or a selected surface structure, at least on the inner face of the base;
 ii) inserting the beaker-shaped inserts into wells of multiwell plates of appropriate dimensioning so that the outer face of the beaker base points towards the inner face of the base of a well of the multiwell plate;
 iii) culturing the cells in the lumen of the beaker-shaped inserts.

The use of a beaker-shaped insert enables testing on the basis of conventional multiwell plates of the cell effects and/or cultivation of the cells with respect to a material and/or a surface structure without interference by foreign materials. The solution to the problem in accordance with the invention consists in providing and inserting a beaker-shaped insert which is dimensioned in such a way that it fits into the well of a commercially available, standardised multiwell plate. The beaker-shaped insert has a selected material and/or a selected surface structure, at least on the inner face of the base. The geometry of the beaker-shaped insert can be adapted to the requirements of the cells, both in the x-y direction (for example forming a circular, star-shaped or differently shaped area of the insert) and in the z-direction. The x- and y-directions describe the expansion of the insert in a two-dimensional plane parallel to the plane in which the openings of the wells of the multiwell plates are arranged, whilst the z-direction describes the direction of the extension of depth of the wells of the multiwell plate. This beaker-shaped insert provides a precisely defined surface which can be produced in chemically and physically modified form. It is thus ensured that the cells are exposed during the culture to only one material exclusively: the material to be tested. The beaker-shaped insert cannot float during culture in the multiwell plate, since the cells are cultivated in the lumen of the beaker-shaped insert. The beaker-shaped insert can be transferred into another cell culture carrier without difficulty, since it is removable. Since the beaker-shaped insert is adapted to the dimensions of commercially available standardised multiwell plates, the equipment for cell cultivation normally already provided in a laboratory can continue to be used without limitation. The properties of suitability for sterilisation, examination under microscope, and reproduction are also provided in such a system. The use of different materials and/or surface structures in the form of beaker-shaped inserts for conventional multiwell plates allows the use of standardised test methods or systems and is thus more time-saving and cost-saving than the complex fixing of material samples using aids in wells of multiwell plates. The use of different materials and/or surface structures in the form of beaker-shaped inserts for conventional multiwell plates enables automated use within the scope of applications of a high-throughput nature. Due to the simple transfer of the beaker-shaped inserts from a well of a first multiwell plate into another well, possibly of another, second, multiwell plate, the test procedure can be extended and/or changed in a versatile manner. Comparable cell culture conditions can be assumed within a single multiwell plate. This reduces the systematic errors of the test runs.

Only small amounts of the new material are typically available at the start of development of new polymer systems. Since the amount required for production of beaker-shaped inserts is less than the amount required for the production of an entire multiwell plate, minimal amounts of new materials can also be used effectively and supplied for testing on the basis of the present invention.

The method according to the invention is a method for testing different selected materials and/or surface structures for the culture of cells and/or microorganisms. The term "cells" is to be understood to mean individual cells and a plurality of cells of one type, or mixtures of cells of different types, as well as united cell structures and tissue parts and/or organ parts. The cells can be of primary origin or cell lines, immortalised cells or any type of mixtures thereof can be used. The cells may comprise or consist of eukaryotic cells, but may also comprise or consist of prokaryotic cells. In this context, microorganisms are understood to be single-cell beings, in particular bacteria and fungi, such as yeasts and algae.

The different selected materials are materials which are basically not water-soluble in processed form and which are present in solid form under normal cell culture conditions, for example in a temperature range of 0° C. to 60° C. The materials are preferably polymer materials, for example homopolymers or copolymers, wherein the polymer materials can be subjected to further treatments and/or modifications after polymerisation.

The different selected surface structures are surfaces of solids which may differ for example in terms of the material composition, three-dimensional form, surface potential, porosity, microstructuring and/or macrostructuring, hydrophobicity, hydrophilicity and/or provision of functional groups. The solids may be either known solid materials or new solid materials. For example, the selected surface structures can be produced by modification of surfaces which already exist.

In the method according to the invention, the materials and/or surface structures to be tested are provided in the form of beaker-shaped inserts. The beaker-shaped inserts are dimensioned in such a way that each beaker-shaped insert can be inserted in a substantially accurately fitting manner into a well of a multiwell plate suitable for cell culture. A multiwell plate suitable for cell culture is understood to mean those, possibly commercially available, standardised cell culture carriers which have a plurality of independent compartments on a single carrier for receiving and culturing cells. A multiwell plate normally has a base which comprises a plurality of separate wells for the culture of cells and a cover which is generally formed in such a way that it can cover all wells of a multiwell plate. These multiwell plates are normally made of a polymer, in particular of polystyrene. Multiwell plates are preferably used in 4-well, 6-well, 12-well, 24-well, 48-well, 96-well or 384-well design, and a 24-well multiwell plate is preferably used. The wells of the multiwell plates can have a base which is either planar or curved, and multiwell plates of which the wells have a planar base are preferably used. Suitable multiwell plates are offered and sold by a range of commercial manufacturers, for example by Corning Inc., BD Biosciences, Biochrom AG, Greiner GmbH, and Nunc GmbH & Co. KG.

In the method according to the invention, at least part of the beaker-shaped inserts can be dimensioned in such a way that a beaker-shaped insert can be inserted in a substantially accurately fitting manner into a well of a 4-well, 6-well, 12-well, 24-well, 48-well, 96-well or 384-well multiwell plate, preferably into a well of a 24-well multiwell plate.

The beaker-shaped inserts are formed and dimensioned in such a way that a beaker-shaped insert can be inserted in a substantially accurately fitting manner into a well of a multiwell plate. Insertion in an accurately fitting manner is understood to mean that the beaker-shaped manner can be inserted into the well in such a way that the beaker-shaped insert does not have so much clearance in the well that the beaker-shaped insert could overturn with moderate shaking. In particular, the beaker-shaped insert is dimensioned in such a way that the beaker-shaped insert can be arranged upright in the well. The gap between the outer wall of the beaker-shaped insert and an inner surface of a side wall of the well is preferably no more than 5 mm at its narrowest point, preferably no more than 1 mm, and the outer wall of the beaker-shaped insert more preferably contacts an inner surface of a side wall of the well in a region, this region possibly having a radial expansion. The actual design and dimensioning of the beaker-shaped inserts are determined by the design and dimensioning of the wells of the multiwell plate to be used.

The beaker-shaped insert has an opening, beaker walls and a base, wherein the walls and the base define the lumen of the insert in question, which is accessible through the opening. The walls and base of the beaker-shaped inserts are liquid-tight, and therefore a lumen is formed to which liquid can only be supplied and/or removed via the opening. The thickness of the walls and/or the base of a beaker-shaped is/are selected in such a way that the beaker-shaped insert has sufficient stability to retain its form in a self-supporting manner, and a sufficient lumen is provided so that cell culture can take place. The form of the outer surface and of the inner surface of the base can either be substantially planar or curved, independently of one another. In this regard, the term "substantially" means that at least 75% of the surface in question has the corresponding property. Both the inner surface and the outer surface are preferably substantially planar. A base which has a substantially planar inner and/or outer surface may also be curved at the edge regions, that is to say the regions where the base contacts the walls of the beaker-shaped insert.

The beaker-shaped insert can have different basic forms and may, but does not have to, follow the form of the corresponding well, provided the beaker-shaped insert can be inserted in a substantially accurately fitting manner. For example, the opening, the body and/or the base of a beaker-shaped insert can be circular, elliptical, star-shaped, or formed otherwise, regularly or irregularly and symmetrically or asymmetrically.

The beaker-shaped insert may have a depth which, on the one hand, is defined by the depth of the corresponding well of the multiwell plate to be used and which, on the other hand, ensures a sufficient lumen in the beaker-shaped insert so that cell culture in the lumen is possible. The depth and design of the base of the beaker-shaped insert are preferably selected and matched to the corresponding depth in such a way that, once inserted successfully, the base of the beaker-shaped insert rests in a planar manner on the base of the well. With this design and on the condition that the beaker-shaped insert and the multiwell plate used are transparent, optimal suitability for examination under microscope with regard to the inner surface of the base of the beaker-shaped insert used is provided and ensured. In the method according to the invention, at least part of the beaker-shaped inserts is preferably transparent.

An embodiment of the beaker-shaped insert is also possible in such a way that the inner dimensions such as diameter, height and volume correspond to those of a well of a multiwell plate having the next higher number of wells. The available cell culture area and the ratio of surface to volume is thus directly comparable to that of a well of a multiwell plate having the next higher well number.

In the method according to the invention, at least part of the beaker-shaped inserts may be transparent.

In the method according to the invention, at least part of the beaker-shaped inserts may be dimensioned in such a way that, once the beaker-shaped inserts have been inserted into a well of a multiwell plate, the beaker base of each insert rests in a planar manner on the base of the well.

The beaker-shaped inserts for use in the method according to the invention may have means which ensure that the beaker-shaped insert is fixed in a well of a multiwell plate. Fixing is understood to mean that, once inserted successfully in a well, the insert remains substantially in its position and cannot be moved further, at least in one direction. To this end, the beaker-shaped insert may have projections at the upper beaker edge which contact the upper edge of the well once the beaker-shaped insert has been inserted and thus prevent further penetration or sinking of the insert into the well.

In the method according to the invention, at least part of the beaker-shaped inserts can have means which ensure the fixing of the beaker-shaped insert in a well of a multiwell plate, and at least part of the beaker-shaped inserts preferably has projections at the upper beaker edge which contact the upper edge of the well once the beaker-shaped insert has been inserted.

The beaker-shaped inserts each have a selected material and/or a selected surface structure, at least on the inner face of the base of the insert. Beaker-shaped inserts in which the respective selected material and/or the respective selected surface structure is provided over the entire inner surface of the beaker-shaped insert or over the surface of the beaker-shaped insert facing the lumen of the insert are preferably used. However, such beaker-shaped inserts in which only the beaker base comprises or consists of the respective selected material and/or the respective selected surface structure can also be used. The entire beaker-shaped insert particularly preferably consists of the selected material to be tested.

In the method according to the invention, at least some of the beaker-shaped inserts may comprise the respective selected material and/or the respective selected surface structure over the entire inner surface of the beaker-shaped insert.

In the method according to the invention, at least some of the beaker-shaped inserts can be formed in such a way that only the beaker base comprises or consists of the respective selected material and/or the respective selected surface structure.

In the method according to the invention, at least some of the beaker-shaped inserts may consist of the respective selected material.

Depending on the type and nature of the material to be tested, the beaker-shaped inserts can be produced by known methods. These methods include methods as are used in plastics shaping. For example, hot forming methods can be used, for example injection moulding, transfer moulding, compression moulding, thermoforming and/or foaming. Methods for shaping from solutions can also be used, for example dipping, vacuum casting and/or coating. Other shaping methods can also be applied, such as machining production from a solid material. Different production methods can also be combined, for example injection-compression moulding, internal gas pressure methods, structural foam moulding, microfoaming methods or insert moulding.

Should the material to be tested not be suitable for the production of an entire beaker-shaped insert, it is sufficient if merely the inner surface of the beaker base facing the lumen comprises the material to be tested and/or the surface structure to be tested. To this end, the material to be tested can be supplied to a beaker-shaped insert, for example by means of back injection.

In principle, the type of production of the beaker-shaped insert is irrelevant to the method according to the invention. Methods which allow the production of the beaker-shaped inserts without the use of solvents are preferably used. For example, such methods include methods for hot forming or melt processing, such as injection moulding, transfer moulding, compression moulding and thermoforming.

In the method according to the invention, at least part of the beaker-shaped insert can be produced by means of a back injection method.

For example, in the method according to the invention, the beaker shaped insert can be subjected to a surface modification following production thereof, so as to provide the surface structures to be tested where necessary. These surface modifications may include modifications produced by chemical reactions, such as the introduction of functional groups which change at least one property of the treated surface, and plasma treatments and/or other methods for physical surface modification. Physical methods include such methods in which at least one luminal surface of the insert is treated with a component which acts as a solvent for the used material of the insert, followed by the addition of a component which constitutes a precipitating agent for the solution produced. Such a treatment not only changes the surface morphology of the beaker, but can open up additional possibilities for further surface modifications where necessary, for example by subsequent chemical modifications. Methods are also included in which gases in the supercritical state, preferably supercritical $CO_2$, are used, for example by foaming processes, to produce surface modifications. Surface structures can also be produced merely by the production method used for the beaker-shaped inserts, for example in the case of back injection. Laser methods or other methods can also be used for selective material removal. Lastly, combinations of different methods for surface modification may also be included.

Beaker-shaped inserts with surfaces having varying parameters, for example in terms of the material composition at the surface, surface potential, porosity, microstructuring and/or macrostructuring, hydrophobicity, hydrophilicity and/or provision of functional groups, can be provided by such surface modifications and supplied for testing.

In the method according to the invention, at least one beaker-shaped insert may have a surface structure on the inner face of the beaker which is only produced once the beaker-shaped insert has been formed.

In the method according to the invention, the beaker-shaped inserts are each inserted into a well of multiwell plates of corresponding dimension so that the outer face of the beaker base points towards the inner face of the base of the respective well of the multiwell plate.

It is thus ensured that, once inserted successfully, the lumen of the beaker-shaped inserts remains accessible from the outside via the opening so that the components can be supplied for cell culture.

In a further step of the method according to the invention, cells are then cultured in the lumen of the beaker-shaped inserts inserted into the relevant wells. The conditions for cell culture and the parameters for assessment of the obtained test results depend on the respective question to be investigated. The method according to the invention is not restricted to the culture of specific cells or the testing of specific materials or selected conditions, but is suitable for a multiplicity of applications.

The present invention relates to a kit for carrying out a method according to the invention, wherein the kit is characterised in that the kit includes a plurality of different beaker-shaped inserts as described above in greater detail. The number of beaker-shaped inserts contained in a kit can preferably be divided by the number of wells of a multiwell plate, the beaker-shaped inserts being matched to the dimensions of said multiwell plate. The kit may also include a description of the materials and/or surface structures which are provided by the beaker-shaped inserts of the kit.

BRIEF DESCRIPTION OF THE DRAWINGS

Figures

FIG. 1 shows an embodiment of a beaker-shaped insert for use with a 24-well multiwell plate manufactured by Corning Inc., USA, wherein a perspective plan view is illustrated in (A), a side view is illustrated in (B), a view showing a sectional plane A-A is illustrated in (C), and a schematic sectional view along the sectional plane A-A is illustrated in (D).

The invention will be explained in greater detail hereinafter on the basis of practical examples.

DETAILED DESCRIPTION OF THE PRESENTLY PREFERRED EMBODIMENTS

Examples

Design of a Beaker-Shaped Insert for a 24-Well Multiwell Plate Manufactured by Corning Inc., USA:

The beaker-shaped insert illustrated schematically in FIGS. 1(A) to (D) has an opening 1, a peripheral wall 2 and a base 3. The insert has the basic form of a conical frustum, wherein the area of the opening 1 is larger than the area of the base 3. At the end of the insert facing away from the base 3, the insert has a projection which is used to fix the insert in the well. The base 3 is substantially planar and has a polished outer surface. On the inner surface facing the lumen, the base 3 comprises a material to be tested. The depth of the insert is selected in such a way that, once inserted successfully into a well of a 24-well multiwell plate by Corning Inc., the base 3 of the insert rests in a planar manner on the base of the well. If both the insert and the multiwell plate are transparent, cells which grow on the inner surface of the base of the insert can thus be examined using conventional microscopes normally used in cell preparation (for example inverted microscopes).

The invention claimed is:

1. A method for testing different selected materials or surface structures for the culture of cells or microorganisms, said method comprising the following steps:
   i) providing a plurality of different selected materials or surface structures to be tested in the form of beaker-shaped inserts, wherein the beaker-shaped inserts are dimensioned in such a way that each beaker-shaped insert can be inserted in a fitting manner into a well of a multiwell plate, wherein each beaker-shaped insert has walls, a base, and an opening in the side facing away from the base, wherein the walls and base of the beaker-shaped inserts are permanently joined to be liquid-tight, and wherein each beaker-shaped insert has a selected material or a selected surface structure on at least a portion of the inner face of the base;
   ii) inserting the beaker-shaped inserts into wells of multiwell plates so that an outer face of the base of the beaker-shaped insert points towards the inner face of the base of a well of the multiwell plate;
   iii) culturing the cells at least on the inner surface of the base of the beaker-shaped inserts.

2. The method according to claim 1, wherein at least part of the beaker-shaped inserts is dimensioned in such a way that a beaker-shaped insert can be inserted in a fitting manner into a well of a 4-well, 6-well, 12-well, 24-well, 48-well, 96-well or 384-well multiwell plate.

3. The method according to claim 1, wherein some of the beaker-shaped inserts have means which ensure that the beaker-shaped insert is fixed in a well of a multiwell plate.

4. The method according to claim 1, wherein at least part of the walls or base of the beaker-shaped inserts is transparent.

5. The method according to claim 1, wherein the beaker-shaped inserts are dimensioned in such a way that, once inserted into a well of a multiwell plate, the base of the beaker-shaped insert rests in a planar manner on the base of the well.

6. The method according to claim 1, wherein at least some of the beaker-shaped inserts comprise the selected material or the selected surface structure over the entire inner surface of the walls and base of the beaker-shaped insert.

7. The method according to claim 1, wherein some of the beaker-shaped inserts consist of the selected material.

8. The method according to claim 1, wherein some of the beaker-shaped inserts are formed in such a way that only the beaker base comprises or consists of the respective selected material or the selected surface structure.

9. The method according to claim 8, wherein at least part of the walls or base of the beaker-shaped insert is produced by means of a back injection method.

10. The method according to claim 1, wherein an beaker-shaped insert has a surface structure on the inner face of the beaker which is only produced once the beaker-shaped insert has been formed.

11. A kit for carrying out a method according to claim 1, wherein the kit comprises a multiplicity of beaker-shaped inserts having a different selected material or selected surface structure on at least a portion of the inner face of the base.

* * * * *